United States Patent
Mondain-Monval et al.

(10) Patent No.: US 6,866,838 B1
(45) Date of Patent: Mar. 15, 2005

(54) COMPOSITE NANOSPHERES AND THEIR CONJUGATES WITH BIOMOLECULES

(75) Inventors: Olivier Mondain-Monval, Bordeaux (FR); Abdelhamid Elaissari, Lyons (FR); Eric Bosc, Salles (FR); Christian Pichot, Corbas (FR); Bernard Mandrand, Villeurbanne (FR); Jérôme Bibette, Bordeaux (FR)

(73) Assignees: Bio Merieux, Marcy l'Etoile (FR); Centre National de la Recherche Scientifique, Paris (FR)

( * ) Notice: Subject to any disclaimer, the term of this patent is extended or adjusted under 35 U.S.C. 154(b) by 221 days.

(21) Appl. No.: 10/129,141

(22) PCT Filed: Nov. 6, 2000

(86) PCT No.: PCT/FR00/03085

§ 371 (c)(1),
(2), (4) Date: Jul. 29, 2002

(87) PCT Pub. No.: WO01/33223

PCT Pub. Date: May 10, 2001

(30) Foreign Application Priority Data

Nov. 5, 1999 (FR) .............................. 99 14194

(51) Int. Cl.$^7$ ............................ A61B 8/00; A61K 9/14; B01J 13/02
(52) U.S. Cl. ...................... 424/9.52; 424/189; 424/490; 424/496; 424/497; 264/4; 264/4.1; 264/4.3; 264/4.32; 428/402; 428/402.2; 428/402.22
(58) Field of Search ............................ 424/9.52, 9.51, 424/489, 490, 496, 497; 516/20, 53, 77; 264/4, 4.1, 4.3, 4.32, 4.33, 4.7; 428/402, 402.2, 402.21, 402.22

(56) References Cited

U.S. PATENT DOCUMENTS

| | | | |
|---|---|---|---|
| 4,157,323 A | * 6/1979 | Yen et al. | ...................... 522/84 |
| 4,342,739 A | 8/1982 | Kakimi et al. | |
| 4,358,388 A | 11/1982 | Daniel et al. | |
| 5,922,304 A | * 7/1999 | Unger | .......................... 424/9.3 |
| 6,416,740 B1 | * 7/2002 | Unger | ....................... 424/9.52 |

FOREIGN PATENT DOCUMENTS

| | | |
|---|---|---|
| EP | 0 180 384 A2 | 10/1985 |
| EP | 0 390 634 A1 | 3/1990 |
| WO | WO 97/34909 | 9/1997 |
| WO | WO 99/19000 A1 | 4/1999 |
| WO | WO 99/35500 | 7/1999 |

* cited by examiner

Primary Examiner—Michael G. Hartley
(74) Attorney, Agent, or Firm—Oliff & Berridge, PLC

(57) ABSTRACT

The invention concerns composite nanospheres having a diameter ranging between about 50 and 1000 nm plus or minus 5%, preferably between about 100 and 500 nm plus or minus 5% and advantageously between 100 and 200 nm plus or minus 5%, and comprising an essentially liquid core consisting of an organic phase and inorganic nanoparticles, distributed inside the organic phase, and a skin consisting of at least a hydrophilic polymer derived from the polymerisation of at least one water soluble monomer, in particular N-alkylacrylamide or a N—N-dialkylacrylamide; conjugates derived from said nanospheres; their preparation methods and their uses.

21 Claims, No Drawings

COMPOSITE NANOSPHERES AND THEIR CONJUGATES WITH BIOMOLECULES

Microencapsulation is a method used for producing small solid particles coated with at least one polymer layer. This method has in particular been used for producing inorganic powders coated with a layer of an organic polymer. Such systems are supposed to have properties different from the sum of the properties of the individual components, in particular better mechanical properties. Microencapsulation methods have in particular been used in the field of the preparation of pigments, inks, plastics and paints. One of the most important applications of encapsulated particles and pigments is found in the field of emulsion paints. However, when the inorganic particles obtained by encapsulation are magnetizable, that opens particular routes in the field of biology, for example by virtue of the coupling of proteins or of antibodies with the encapsulated particles for use in diagnostic tests. Such particles are also used in methods of biochemical separation. In general, the encapsulated particles are of interest as a support, vector or vehicle in the fields of biological engineering, diagnostics and pharmacy. To this effect, they have been used in medical diagnostics as solid support for biological macromolecules.

Colloidal particles exhibit several advantages relative to traditional solid supports, such as tubes and plates, in particular because they make it possible to have a large surface for specific interactions and because they can be easily chemically modified in order to introduce, at their surface, functional groups capable of reacting with other molecules, for example biological molecules such as antibodies or antibody fragments, proteins, polypeptides, polynucleotides, nucleic acids, nucleic acid fragments, enzymes or chemical molecules such as catalysts, medicaments, cage molecules or chelators.

Among colloidal particles, magnetic latexes have attracted great interest in the analytical field and are used, for example, as a means for separating and/or detecting analytes, such as antigens, antibodies, biochemical molecules, nucleic acids and the like.

Composite particles of the polymeric/magnetic type are usually classified into three categories on a size criterion: small particles having a diameter of less than 50 nm, large particles having a diameter greater than 2 $\mu$m and intermediate particles having a diameter of between 50 and 1000 nm.

However, for them to be considered as good candidates, in particular for a diagnostic application, they must meet certain criteria. From a morphological point of view, it is preferable for them to be relatively spherical and for the magnetic charge to be distributed relatively homogeneously in the polymer matrix. They should not aggregate in an irreversible manner under the action of a magnetic field, which means that they can be easily, rapidly and reversibly redispersed. Likewise, they should have a relatively low density in order to reduce the phenomenon of sedimentation. Advantageously, they should have a narrow particle size distribution. The particles are also said to be monodisperse or isodisperse.

Thus, because of their size and their density, the large magnetic particles in suspension in a liquid phase tend to rapidly sediment. Moreover, they tend to form aggregates after being subjected to a magnetic field because they are likely to have thereby been made permanently magnetized. The expression residual magnetization is used. They do not therefore constitute a good candidate.

Conversely, small magnetic particles tend to remain in suspension because of their Brownian movement and are attracted with difficulty, or even not at all, by a magnet, in particular if the applied magnetic field is relatively weak. They are not therefore very appropriate for the uses developed above.

There is therefore an obvious advantage in producing composite particles of the polymeric/magnetic type, having an intermediate size of between 50 and 1000 nm, which both overcomes the above-mentioned disadvantages and meet in particular the criteria established above. However, the invention is not limited to composite magnetizable particles, as described below.

There may be mentioned Dynal particles (trade name). These particles are microspheres consisting of a porous core of polystyrene and iron oxides, the iron oxides having been deposited by impregnation in the pores available at the surface of the polystyrene, and of an envelope made of another polymer which encapsulates the iron oxides of the porous microspheres. They have a diameter of 2.8 $\mu$m (particles M280) and 4.5 $\mu$m (particles M450), respectively, and are relatively uniform in size. They are therefore considered as isodisperse particles, but because of their high size, exhibit the above-mentioned disadvantages, mainly the phenomenon of sedimentation. Furthermore, their specific surface area is low.

Patent application EP 0 390 634 describes magnetizable composite microspheres of hydrophobic crosslinked vinylaromatic polymer having a diameter of the order of 50 to 10 000 nm and comprising a solid core consisting of magnetizable particles and a skin consisting of a hydrophobic copolymer derived from at least one hydrophobic vinylaromatic monomer and from at least one polyethylenically unsaturated emulsifying polymer soluble in the vinylaromatic monomer(s) and capable of crosslinking with said monomer(s). However, although they can meet the size requirement, they have the disadvantage of not having a uniform distribution of the magnetic charge which is located inside the core. Moreover, and as is evident from the appended figures in this patent, the particles are not homogeneous in size. They are therefore a set of polydisperse particles which have to be fractionated so that only the particles of the expected size are selected. Finally, because the magnetizable particles inside the solid core are oriented in a random and stiff manner in their orientation, the magnetic moment resulting from the composite microspheres therefore corresponds to the algebraic sum of the moments of the magnetizable particles with, as a consequence, a reduction in the resulting moment linked to this random distribution of the particles inside the solid core.

As will be seen below, one of the characteristics of the composite nanospheres of the invention, when they are magnetic, is that the nanoparticles dispersed inside the essentially liquid core are sufficiently mobile for their resulting magnetic moment to facilitate a separation under the action of a magnetic field, even a weak magnetic field, which has an indisputable advantage compared with the magnetic particles with a solid core of the type described in patent application EP 0 390 634. This is particularly advantageous when the content of magnetic nanoparticles is low.

The invention therefore relates to novel encapsulated composite nanospheres which overcome the abovementioned disadvantages.

The encapsulated composite nanospheres of the invention contain, in their core, a load of inorganic material uniformly distributed inside the core; they are isodisperse in size and are capable of being used in fields as diverse as biology, in particular for diagnostics, the preparation of paints, inks and the like.

The composite nanospheres of the invention have a diameter of between about 50 and 1000 nm plus or minus 5%, preferably between about 100 and 500 nm plus or minus 5% and advantageously between 100 and 200 nm plus or minus 5%, and comprise:

an essentially liquid core consisting of an organic phase and of inorganic nanoparticles homogeneously distributed inside the organic phase, and an envelope consisting of at least one hydrophilic polymer which is derived from the polymerization of at least one water-soluble monomer, in particular an N-alkylacrylamide, an N,N-dialkylacrylamide and more particularly N-isopropylacrylamide (NIPAM), N-methylacrylamide, N-ethylmethacrylamide, N-n-propylacrylamide, N-n-propylmethacrylamide, N-isopropylmethacrylamide, N-cyclopropylacrylamide, N,N-diethylacrylamide, N-methyl-N-isopropylacrylamide, N-methyl-N-n-propylacrylamide.

Plus or minus 5% means that the mean diameter by volume is defined to within plus or minus about 5%. The size is measured by light scattering.

The essentially liquid core comprises:

(i) an aliphatic or cyclic hydrocarbon chosen from compounds comprising from 5 to 12 carbon atoms, isomers thereof and mixtures thereof. Preferably, the hydrocarbon is chosen from pentane, hexane, heptane, octane, nonane, decane, undecane and dodecane, it being understood that it is within the capability of persons skilled in the art to adapt the polymerization conditions of the method of production as a function of the choice or of the hydrocarbon(s) selected. In particular, when the polymerization is carried out by a high temperature, the reaction setup should be adapted to volatile hydrocarbons, such as pentane, and to the nature of the polymerization initiator chosen, (ii) inorganic nanoparticles chosen from metal oxides of iron, titanium, cobalt, zinc, copper, manganese, nickel; magnetite; hematite, ferrites such as manganese, nickel and manganese-zinc ferrites; alloys of cobalt, nickel; zeolites; talc; clays such as bentonite and kaolin; alumina; silica; graphite; carbon black or other inorganic materials. Preferably, the inorganic materials are chosen from metal oxides of iron, titanium, cobalt, zinc, copper, manganese, nickel; magnetite; hematite; ferrites such as the ferrites of manganese, nickel, manganese-zinc; alloys of cobalt, nickel.

The core thus defined may furthermore comprise a marker, such as a fluorescent, luminescent or radioactive marker, it being understood that the marker is introduced during the preparation of the emulsion as described in Example 1 which follows.

The inorganic nanoparticles represent from 5 to 95%, preferably from 10 to 90%, still more preferably from 20 to 80% and advantageously from 50 to 80% by mass relative to the total mass of the composite nanospheres.

In one embodiment of the invention, the envelope comprises a hydrophilic polymer as defined above which constitutes an external layer of said envelope and a hydrophobic polymer which constitutes an internal layer of said envelope, situated at the interface between the external layer of the envelope and the essentially liquid core.

The hydrophobic polymer is chosen from homopolymers of vinylaromatic monomers which are insoluble in water, such as styrene, methylstyrene, ethylstyrene, tert-butylstyrene, vinyltoluene, as well as the copolymers of these monomers with each other and/or with other comonomers, such as alkyl acrylates and alkyl methacrylates in which the alkyl group comprises from 3 to 10 carbon atoms, the esters of ethylenic acids possessing 4 or 5 carbon atoms and alkyl possessing 1 to 8 carbon atoms, methacrylic acids, styrene derivatives, diene compounds.

The composite nanospheres of the invention in particular find applications in the fields of paint, inks, plastics and, when they are functionalized, in various fields of biology, in particular for the separation of biological or biochemical molecules, for diagnostic tests, for the preparation of therapeutic, prophylactic or cosmetic compositions.

Accordingly, in one embodiment of the invention, the composite nanospheres exhibit at the surface of the envelope functional groups capable of interacting with molecules, for example biological molecules, said functional groups being provided (i) either by a surface treatment of the envelope, for example a chemical treatment such as hydrolysis or grafting of functional groups, (ii) or by addition of at least one functional monomer, such as methacrylic acid, acrylic acid, itaconic acid, aminoethyl methacrylate, aminopropyl methacrylamide, (iii) or by addition of a functional initiator, such as dimethyl 2,2'-azobis(2-methylpropionate), 4,4'-azobis(4-cyanovaleric acid) and 2,2'-azobis(2-cyanopropanol).

The composite nanospheres thus functionalized may be used for the concentration of nucleic acids according to the protocol described in patent application EP 0 842 184 or for the concentration of proteins in accordance with the protocol described in patent application WO 99/35500.

Thus, the composite nanospheres of the invention may be functionalized and exhibit at the surface of the envelope reactive functional groups such as carboxyl, amine, thiol, hydroxyl, tosyl or hydrazine groups, which are capable of reacting with at least one ligand.

The functionalized composite nanospheres thus formed will be capable of immobilizing a ligand, for example a biological molecule, such as an antibody, an antibody fragment, a protein, a polypeptide, an enzyme, a polynucleotide, a probe, a primer, a nucleic acid fragment; chemical molecules, such as chemical polymers, medicinal substances, cage molecules, chelating agents, catalysts, biotin.

The subject of the present invention is also conjugates derived from the composite nanospheres of the invention coupled to at least one ligand as defined above and their uses.

By way of example, said conjugates are used in immunological tests for the detection and/or quantification of proteins, antigens, antibodies in a biological sample or in tests using probe technology for the detection and/or quantification of a nucleic acid or of a nucleic acid fragment in a biological sample. The use of probes for the detection and/or quantification of a nucleic acid in a sample is well known to a person skilled in the art and there may be mentioned, by way of illustration, the sandwich hybridization technique. Likewise, the conjugates of the invention may be used as "primer-carrying agents" for a nucleic acid amplification reaction in a sample, for example by PCR (Polymerase Chain Reaction) or any other appropriate amplification technique, thus allowing the detection and/or the quantification of nucleic acids in the biological sample.

The subject of the present invention is therefore also a diagnostic reagent and a diagnostic composition comprising, inter alia, said composite nanospheres or said conjugates and the use of said reagent in an analytical test, for example for the concentration of proteins or nucleic acids or alternatively in a diagnostic test.

The conjugates also find application in the therapeutic or prophylactic field as vehicle or vector for a medicinal substance, a defective gene repair agent, an agent capable of blocking or inhibiting the expression of a gene, such as an antisense probe in therapy, or an agent capable of blocking or inhibiting the activity of a protein, and thereby they can be used in a therapeutic or prophylactic composition.

Thus, the conjugates of the invention are capable of carrying a medicinal substance in a therapeutic or prophylactic composition which comprises said conjugate in combination with an appropriate and pharmaceutically acceptable adjuvant and/or diluent and/or excipient, said medicinal substance being capable of being released in vivo. The definitions of pharmaceutically acceptable excipients and adjuvants are described, for example, in Remingtons's Pharmaceutical Sciences 16$^{th}$ ed., Mack Publishing Co.

The conjugates of the invention are also capable of carrying a gene of therapeutic interest encoding at least one protein of interest or a fragment of a protein of interest, it being understood that the term protein is understood to mean both a protein in its most generally used definition and an antibody. Of course, such a conjugate is incorporated into a therapeutic or prophylactic composition which also comprises the components necessary for the expression of said gene of therapeutic interest.

The conjugates of the invention can also be used, when incorporated into a therapeutic or prophylactic composition, for the in vivo transfer of antisense oligonucleotides or probes. The antisense molecules are capable of specifically interfering with the synthesis of a target protein of interest, by inhibiting the formation and/or the function of the polysome according to the position of the mRNA in the target. The frequent choice of the sequence surrounding the initiation codon for translation as target for inhibition by an antisense oligonucleotide is therefore designed to prevent the formation of the initiation complex. Other mechanisms in the inhibition by antisense oligonucleotides involve activation of ribonuclease H which digests the antisense oligonucleotide/mRNA hybrids or interference at the splicing sites by antisense oligonucleotides whose target is an mRNA splicing site. The antisense oligonucleotides also have complementary DNA sequence and can therefore interfere in transcription through the formation of a triple helix, the antisense oligonucleotide binding via so-called Hoogsteen hydrogen bonds in the large spiral of the DNA double helix. In this particular case, reference is made more precisely to antigenic oligonucleotides. It is clearly understood that the antisense oligonucleotides may be strictly complementary to the DNA or RNA target to which they have to hybridize, but also not strictly complementary provided that they hybridize to the target. Likewise, this may include antisense oligonucleotides not modified or modified in the internucleotide bonds. All these notions are part of the general knowledge of persons skilled in the art.

The present invention therefore relates to a therapeutic composition comprising, inter alia, a vector conjugate for an antisense oligonucleotide as defined above.

Finally, the conjugates are also capable of forming complexes of the cage molecule/cryptate or chelator/chelated molecule type or of serving as vehicle for catalysts in a chemical application.

The composite nanospheres and the conjugates of the invention are obtained by a method of encapsulation via polymerization of an emulsion according to the protocol described in the examples which follow and the invention also relates to such a method of preparation.

According to the method of the invention, (i) a stable and isodisperse starting emulsion is available consisting of two imiscible phases, a hydrophobic phase A consisting of droplets containing inorganic nanoparticles homogeneously dispersed in an organic phase containing a surfactant, said phase A being dispersed in a hydrophilic phase B, (ii) at least one water-soluble monomer, one water-soluble crosslinking agent and one water-soluble polymerization initiator are introduced into the hydrophilic phase B, and (iii) the water-soluble monomer is polymerized in the presence of the crosslinking agent and the initiator.

In one embodiment of the invention, prior to step (ii), at least one hydrophobic monomer and a first water-soluble polymerization initiator is introduced into the hydrophilic phase, and then the addition to the hydrophilic phase of at least the water-soluble monomer and the crosslinking agent and optionally, if necessary, a second water-soluble polymerization initiator which is identical to or different from the first initiator is carried out, it being understood that the addition of a second polymerization initiator is only useful if the quantity of the first polymerization initiator is limited or insufficient to drive the complete polymerization to completion. The total quantity of initiator is between 1 and 10 mol %, preferably between 1 and 5 mol % relative to the total monomer concentration.

The water-soluble initiator is chosen from peroxydisulfate salts, that is to say persulfates, such as potassium persulfate, sodium persulfate and ammonium persulfate; hydroperoxides, such as cumene hydroperoxide; hydrogen peroxide; 2,2'-azobisamidinopropane hydrochloride, dimethyl 2,2'-azobis(2-methylpropionate), 4,4'-azobis(4-cyanovaleric acid) and 2,2'-azobis(2-cyanopropanol). Among these, dimethyl 2,2'-azobis(2-methylpropionate), 4,4'-azobis(4-cyanovaleric acid) and 2,2'-azobis(2-cyanopropanol) are functional initiators. The persulfates are water-soluble initiators. Decomposition under the action of heat generates anions with sulfate radicals which will contribute toward charging the nanosphere. Hydrogen peroxide decomposes in water to form hydroxyl radicals which are not charged. The hydroperoxides are soluble both in an aqueous phase and in particles consisting of monomers. The decomposition of the hydroperoxides generates a hydroxyl and another oxygenated radical which will become distributed in one of the phases according to the type of peroxide used. Cumene hydroperoxide, in the case of the polymerization of styrene, is supposed to decompose at the interface between the particle of monomers and the water, the hydroxyl radicals enter into the aqueous phase and the nonpolar radicals diffuse toward the particle. On the cationic or anionic nature of the initiator will depend the cationic or anionic character of the composite nanosphere of the invention and of the resulting conjugate.

The initiator agent is introduced into the hydrophilic phase either simultaneously with the introduction of the monomers, or prior to their introduction, or alternatively subsequent to their introduction.

The water-soluble monomer and the hydrophobic monomer correspond to the definitions given above.

The water-soluble crosslinking agent is chosen from N,N'-methylenebisacrylamide (MBA) and ethylene glycol dimethacrylate.

The hydrophobic organic phase A is a phase comprising an aliphatic or cyclic hydrocarbon chosen from compounds comprising from 5 to 12 carbon atoms, isomers thereof and mixtures thereof. In particular, the hydrocarbon is chosen from pentane, hexane, heptane, octane, nonane, decane, undecane and dodecane, it being understood that when the polymerization is carried out by raising the temperature, persons skilled in the art should adapt the reaction setup to volatile components, such as pentane, and to the nature of the polymerization initiator chosen. Phase B is an aqueous phase, such as water.

The polymerization is preferably carried out by raising the temperature up to about 60° C. to about 90° C., preferably to about 70° C., in the presence of the polymerization initiator, it being understood that the polymerization conditions will be determined by persons skilled in the art according to the nature of the initiator chosen; or by photochemistry using rays, such as UV rays or a laser beam or other sources of energy.

EXAMPLE 1

A stable and isodisperse starting emulsion was prepared in accordance with either of the protocols described in this example.

(i) The primary emulsion was prepared using an emulsification method by gradually incorporating, while shearing using a colloid mill (Ika: trade name), the dispersed phase, consisting of 45% by weight of iron oxides in octane, into the continuous phase consisting of sodium dodecyl sulfate at a concentration of 50% by weight in water until fractions containing 80% by weight of organic ferrofluid are obtained. The mixture thus defined was fragmented in a PG398-type Couette at a previously determined shear rate. The primary emulsion thus prepared is a polydisperse emulsion characterized by a wide distribution of the diameter of the droplets which is then treated by successive magnetic sortings for the production of the starting emulsion which is isodisperse in size.

(ii) The primary emulsion was prepared using an emulsification method by rapidly adding the dispersed phase, consisting of octane, 73% by weight of iron oxides and a lipophilic surfactant of the monoglycerol or polyglycerol polyrisinoleate type (1 to 10% by weight), to the continuous phase consisting of tergitol NP10-type surfactant (31% by weight) using a spatula. The mixture thus defined is then fragmented in a PG398-type Couette at a previously defined shear rate. The primary emulsion thus prepared is a relatively isodisperse emulsion characterized by a low distribution of the diameter of the droplets which is then treated by successive magnetic sortings for the production of the starting emulsion which is isodisperse in size.

EXAMPLE 2

20 ml of emulsion (1% by weight dispersed in sodium dodecyl sulfate (SDS) at 0.8 times the critical micell concentration (CMC) and in water) are poured into a 25-ml round-bottomed flask for polymerization. The solution is degassed by bubbling under nitrogen to drive the air out for 9 hours. 24 $\mu$l of styrene monomers and 4.3 mg of solubilized potassium persulfate initiator in 0.4 ml of water are introduced and the mixture is kept stirring for 2 hours. The temperature is then raised to 70° C., with stirring for 20 minutes. The mixture (280 mg of N-isopropylacrylamide solubilized in 1 ml of water, 11 mg of methylene bisacrylamide solubilized in 0.4 ml of water, 30 $\mu$l of methacrylic acid) is introduced over a period of 30 minutes. The polymerization is carried out for 12 hours under a nitrogen atmosphere and at a temperature of 70° C. The presence of functional groups is ensured by methacrylic acid.

The final magnetic latex has the following characteristics at 20° C.: the diameter determined by light scattering is 192 nm plus or minus 5 nm. The iron oxide level is about 75%.

EXAMPLE 3

50 ml of emulsion (0.7% dispersed in SDS at 1 times the CMC and in water) are poured into a 50 ml polymerization reactor. The solution is degassed by bubbling under nitrogen for 3 h 30 min. 7 $\mu$l of styrene monomers and 2 $\mu$l of methacrylic acid are introduced and the mixture is kept stirring for 20 minutes. The initiator (potassium persulfate, 2 mg), solubilized in 0.1 ml of water, is introduced and the solution is homogenized for 10 minutes. The temperature is then raised to 70° C., with stirring for 25 minutes. The following mixture (80 mg of N-isopropylacrylamide solubilized in 0.5 ml of water, 6 $\mu$l of methacrylic acid, 4 $\mu$l of styrene) is introduced as follows:

Introduction of 200 $\mu$l of mixture and homogenization for 30 minutes followed by introduction of 200 $\mu$l of mixture and homogenization for 30 minutes before introducing the other components of the mixture. The polymerization reaction is carried out, with stirring at 300 rpm for 16 hours under a nitrogen atmosphere and at a temperature of 70° C. The presence of functional groups is ensured by methacrylic acid.

The final magnetic latex has the following characteristics: a diameter of 187 nm at 20° C. plus or minus 5 nm determined by light scattering and an iron oxide level of about 70%. Zeta potential −50 mV at pH 10 and 0 mv at pH 4.5.

EXAMPLE 4

15 ml of an emulsion (0.7% dispersed in water at 1 times the CMC in triton X405) are introduced into a 50 ml round-bottomed flask for polymerization. This emulsion is degassed beforehand by bubbling under nitrogen for 5 hours. 7 $\mu$l of styrene monomers and 2 mg of N-(3-aminopropyl)methacrylamide solubilized in 0.2 ml of water are introduced. The mixture $\mu$s homogenized for 25 minutes before introducing 2 mg of 2,2'-azobisamidinopropane hydrochloride, the initiator, solubilized in 0.2 ml of water. After homogenizing for 20 minutes, the temperature is raised to 70° C. for 25 minutes and the following mixture (80 mg of N-isopropylacrylamide solubilized in 0.5 ml of water, 2 mg of methylene bisacrylamide solubilized in 0.1 ml of water, 6 mg of N-(3-aminopropyl)methacrylamide solubilized in 0.1 ml of water) is introduced in the following manner:

Introduction of 0.2 ml of mixture and homogenization for 20 minutes, introduction of 0.2 ml of mixture and homogenization for 30 minutes, introduction of the rest of the mixture.

The polymerization reaction is carried out with stirring, at 300 rpm for 16 hours under a nitrogen atmosphere and at a temperature of 70° C. The presence of amine groups is ensured by N-(3-aminopropyl)methacrylamide.

The final magnetic latex has the following characteristics: a diameter of 187 nm plus or minus nm at 20° C. determined by light scattering and an iron oxide level of the order of 70%. Zeta potential +50 mV at pH 4, −50 mV at pH 10.

EXAMPLE 5

60 $\mu$l of Tween 20 (1%), 636 $\mu$l of phosphate buffer (10 mM at pH 6.9), 60 $\mu$l of N-(3-dimethylaminopropyl)-N'-ethylcarbodiimide dihydrochloride (25 mg/ml), 156 $\mu$l of N-hydroxysulfosuccinimide (25 mg/ml) and streptavidin (48 $\mu$l at 1 mg/ml) are successively added to 240 $\mu$l of a magnetic latex at 3%, obtained as described above.

The mixture is incubated for one hour at room temperature and the particles are then concentrated by applying a magnetic field, and then redispersed in the buffer containing surfactant (10 mM phosphate, pH 6.9+0.05% Tween 20).

9.9 $\mu$l of a biotinylated oligonucleotide (ODN) of 17 mers having a mass of 5753 g/mol at a concentration of 338 nmol/ml) are added to 400 µl of previously synthesized streptavidin-coated particles in order to constitute the positive control. 20 µl of a nonbiotinylated and nonaminated oligonucleotide of 17 mers (mass: 6452 g/mol at a concentration of 167 nmol/ml) are added to 400 µl of previously synthesized streptavidin-coated particles in order to constitute the negative control.

The two controls are incubated for 30 minutes at room temperature, separated three times and redispersed the first time with a basic buffer (10 mM phosphate, pH 9.9+SDS, 5 times the critical micell concentration, the second time with a buffer at neutral pH (10 mM phosphate, pH 6.9+0.05% Tween 20) and the third time in 280 µl of PEG containing salmon sperm DNA.

In both cases, 20 µl of ODN complementary to the ODN of the positive control labeled with horseradish peroxidase (17 mers, concentration 9 nmol/ml) are added.

The two controls are again incubated for one hour at room temperature and are further separated so as to be dispersed again in 400 µl of PEG containing salmon sperm DNA. 50 µl of ortho-phenylenediamine are added to 50 µl of particles. The enzymatic reaction is carried out for 5 minutes and stopped by the addition of 50 µl of sulfuric acid (1M).

The particles are separated from the supernatant and the latter is assayed by a calorimetric method on an Axia Microreader apparatus (trade name, bioMérieux) at 492 and 630 nm.

The positive control gives an optical density of 2000 OD units, whereas the negative control gives a density of 1000 OD units.

The fluctuation in size observed, before and after polymerization in the preceding examples, is attributed to the combination of the following two phenomena: a) a possible evaporation of a portion of the organic phase and b) the conversion of the polymerization from one example to another. The iron oxide level after polymerization is substantially of the same order of magnitude as in the emulsion used before polymerization.

What is claimed is:

1. A method for preparing composite nanospheres, comprising:
introducing at least one water-soluble monomer, at least one water-soluble crosslinking agent and at least one water-soluble polymerization initiator into a hydrophilic phase of a stable isodisperse solution comprising said hydrophilic phase and a hydrophobic phase comprising droplets containing inorganic nanoparticles homogeneous dispersed in an organic phase containing a surfactant, wherein the hydrophobic phase is dispersed in the hydrophilic phase, and the at least one water-soluble monomer is polymerized in the presence of the crosslinking agent and the initiator.

2. The method as claimed in claim 1, wherein at least one hydrophobic monomer and a first polymerization initiator are introduced into the hydrophilic phase before introducing the at least one water-soluble monomer and the at least one water-soluble cross-linking agent.

3. The method as claimed in claim 1, wherein the at least one water-soluble polymerization initiator and a second polymerization initiator are introduced into the hydrophilic phase simultaneously with the addition of the at least one water-soluble monomer and at least one hydrophobic monomer.

4. The method as claimed in claim 1, wherein the at least one water-soluble initiator is selected from the group consisting of peroxydisulfate salts; hydroperoxides; hydrogen peroxide; 2,2'-azobisamidinopropane hydrochloride; dimethyl 2,2'-azobis(2-methylpropionate); 4,4'-azobis(4-cyanovaleric acid); and 2.2'-azobis(2-cyanopropanol).

5. The method as claimed in claim 2, wherein the at least one water-soluble monomer is selected from the group consisting of N-alkylacrylamide and N-N-dialkylacrylamide, and the at least one hydrophobic monomer is selected from the group consisting of vinylaromatic monomers which are insoluble in water, and copolymers of these monomers with each other and/or with other comonomers.

6. The method as claimed in claim 2, wherein the hydrophobic monomer is selected from vinylaromatic monomers which are insoluble in water, and the copolymers of these monomers with each other and/or with other comonomers.

7. The method as claimed in claim 1, in which the at least one water-soluble crosslinking agent is selected from the group consisting of N,N-methylenebisacrylamide (MBA) and ethylene glycol dimethacrylate.

8. The method as claimed in claim 1, wherein the hydrophobic phase comprises an aliphatic and/or cyclic hydrocarbon selected from the group consisting of compounds comprising from 5 to 12 carbon atoms, isomers thereof and mixtures thereof, and the hydrophilic phase is an aqueous phase.

9. The method as claimed in claim 1, wherein the polymerizing step is carried out by at least one of raising the temperature to about 60° C. to about 90° C. in the presence of the polymerization initiator, and photochemistry using rays.

10. The method as claimed in claim 6, wherein the vinylaromatic monomers comprise at least one member selected from the group consisting of styrene, methylstyrene, ethylstyrene, tertbutylstyrene and vinyltoluene.

11. The method as claimed in claim 6, wherein the comonomers are selected from the group consisting of alkyl acrylates and alkyl methacrylates wherein the alkyl group includes from 3 to 10 carbon atoms, esters of ethylenic acids possessing 4 or 5 carbon atoms and of alkyl group possessing 1 to 8 carbon atoms, methacrylic acids, styrene derivatives, and diene compounds.

12. The method as claimed in claim 1, wherein the at least one water-soluble polymerization initiator and a second polymerization initiator are introduced into the hydrophilic phase prior to the addition of the at least one water-soluble monomer and at least one hydrophobic monomer.

13. The method as claimed in claim 2, wherein the at least one water-soluble polymerization initiator and a second polymerization initiator are introduced into the hydrophilic phase subsequent to the addition of the at least one water-soluble monomer and at least one hydrophobic monomer.

14. The method as claimed in claim 4, wherein the peroxydisulfate salts are selected from the group consisting of potassium persulfate, sodium persulfate, and ammonium persulfate.

15. The method as claimed in claim 4, wherein the hydroperoxides include cumene hydroperoxide.

16. The method as claimed in claim 5 wherein the at least one water-soluble monomer is selected from the group consisting of N-isopropylacrylamide, N-methylacrylamide, N-ethylmethacrylamide, N-n-propylacrylamide, N-n-propylmethacrylamide, N-isopropylmethacrylamide, N-cyclopropylacrylamide, N,N-diethylacrylamide, N-methyl-N-isopropylacrylamide, and N-methyl-N-n propylacrylamide.

17. The method as claimed in claim 5, wherein the vinylaromatic monomer is selected from the group consisting of styrene, methylstyrene, ethylstyrene, tert-butylstyrene, and vinyltoluene.

18. The method as claimed in claim 5, wherein the comonomers are selected from the group consisting of alkyl acrylates and alkyl methacrylates wherein the alkyl group includes from 3 to 10 carbon atoms, esters of ethylenic acids comprising 4 or 5 carbon atoms and of alkyl group possessing 1 to 8 carbon atoms, methacrylic acids, styrene derivatives, and diene compounds.

19. The method as claimed in claim 8, wherein the hydrocarbon is selected from the group consisting of pentane, hexane, octane, nonane, decane, and dodecane.

20. The method as claimed in claim 1, wherein at least one hydrophobic monomer, and a first polymerization initiator and a second polymerization initiator are introduced into the hydrophilic phase before introducing the at least one water-soluble monomer and the at least one water-soluble cross-linking agent.

21. The method as claimed in claim 9, wherein the rays comprise at least one member selected from the group consisting of UV rays and a laser beam.

\* \* \* \* \*